United States Patent
Freeman, III et al.

(10) Patent No.: US 7,353,953 B2
(45) Date of Patent: Apr. 8, 2008

(54) PACKAGING OF MULTIPLE FLUID RECEPTACLES

(75) Inventors: Davis Freeman, III, Rochester, NY (US); Robert Novick, Webster, NY (US); Bradley P. Smith, Penfield, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 58 days.

(21) Appl. No.: 10/946,477

(22) Filed: Sep. 21, 2004

(65) Prior Publication Data

US 2005/0079622 A1   Apr. 14, 2005

Related U.S. Application Data

(63) Continuation-in-part of application No. 10/684,536, filed on Oct. 14, 2003, now abandoned.

(51) Int. Cl.
*B65D 69/00* (2006.01)
*B32B 27/12* (2006.01)
*B65B 35/30* (2006.01)
*G01N 1/10* (2006.01)
*G01N 35/02* (2006.01)

(52) U.S. Cl. ............... 206/569; 53/443; 206/431; 206/460; 206/813; 206/820; 356/246; 422/63; 422/66; 422/72; 422/102; 436/48; 436/809

(58) Field of Classification Search ........... 206/569, 206/460, 813, 427, 430–432, 497, 499, 820; 229/87.05; 422/63, 66, 72, 102; 436/48; 436/809; 53/443; 356/246
See application file for complete search history.

(56) References Cited

U.S. PATENT DOCUMENTS 2,548,985 A * 4/1951 Lighter ................. 206/499

(Continued)

FOREIGN PATENT DOCUMENTS

WO   WO 83/00296   2/1983

OTHER PUBLICATIONS

EPSearch Report dated Jun. 26, 2007, Munich, -EP Application No. 04256307.2-2209.

*Primary Examiner*—Bryon P. Gehman
(74) *Attorney, Agent, or Firm*—Todd J Burns

(57) ABSTRACT

Packaged fluid receptacles include: a plurality of fluid receptacles arranged one next to the other to form a composite structure having a top surface, bottom surface and end walls at a first end and a second end and having a longitudinal axis which extends through the end walls; and a removable support which contacts at least the top surface, bottom surface and end walls, the removable support including an attachment for applying a force to remove the support, preferably in a direction along the longitudinal axis. In a preferred embodiment, the support is one-piece and has a single attachment. Preferably, the packaged fluid receptacles are cuvettes usable in a clinical analyzer. A method for inserting a plurality of cuvettes into a clinical analyzer includes: providing packaged cuvettes as described above; inserting the packaged cuvettes into a cuvette loading station of a clinical analyzer in a manner in which the tab remains accessible to application of a force; securing the packaged cuvettes in the loading station; applying a force to the tab to peel back the support from the cuvettes; and removing the support to provide individual cuvettes.

11 Claims, 19 Drawing Sheets

U.S. PATENT DOCUMENTS

| | | | |
|---|---|---|---|
| 2,808,926 A * | 10/1957 | Drake et al. | 206/820 |
| 2,842,261 A * | 7/1958 | Lighter | 206/782 |
| 3,525,428 A * | 8/1970 | Stephan | 206/432 |
| 3,759,374 A * | 9/1973 | Helger et al. | 206/431 |
| 4,263,256 A * | 4/1981 | Morle | 422/66 |
| 4,472,357 A * | 9/1984 | Levy et al. | 422/102 |
| 4,634,575 A | 1/1987 | Kawakami et al. | |
| 4,636,477 A | 1/1987 | Rönka et al. | |
| 4,639,135 A | 1/1987 | Borer et al. | |
| D290,170 S | 6/1987 | Käyhkö | |
| 4,690,900 A | 9/1987 | Kimmo et al. | |
| 4,779,731 A * | 10/1988 | Fujio | 206/432 |
| 4,867,315 A * | 9/1989 | Baldwin | 206/820 |
| 5,067,612 A * | 11/1991 | Tsuchiya et al. | 206/497 |
| 6,328,164 B1 | 12/2001 | Riekkinen et al. | |
| 7,098,035 B2 * | 8/2006 | Riekkinen et al. | 436/43 |

\* cited by examiner

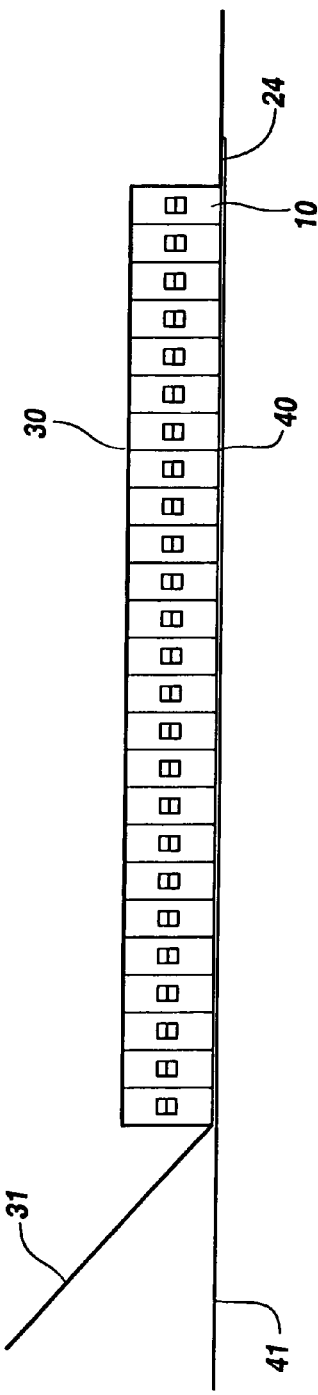
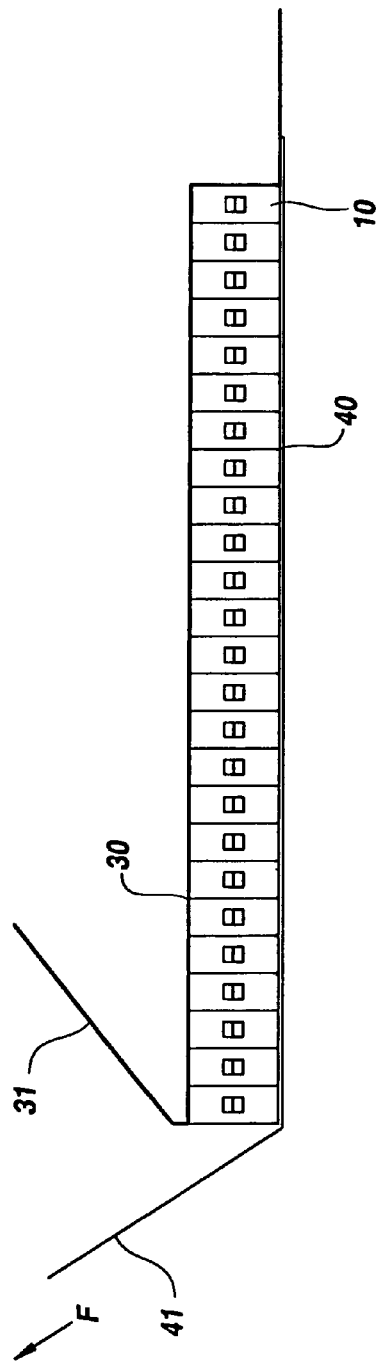

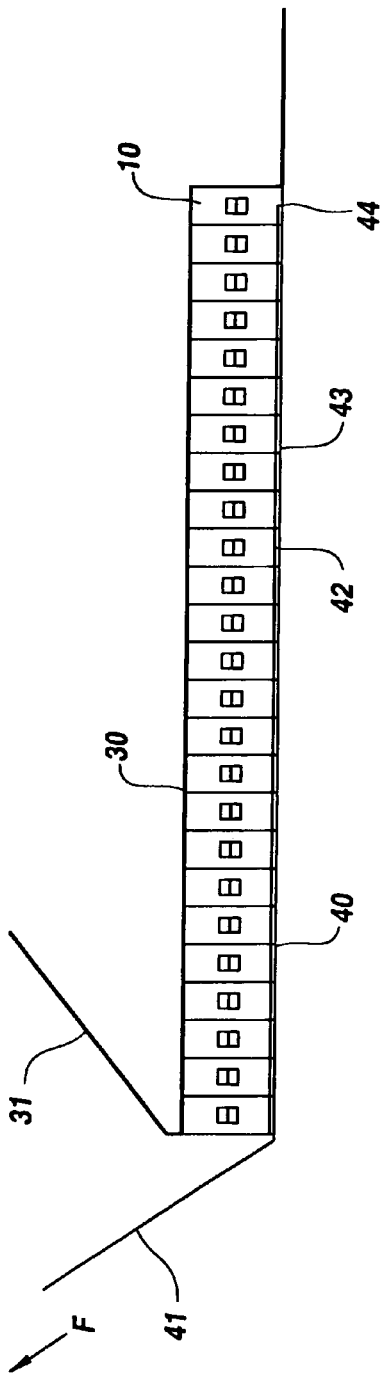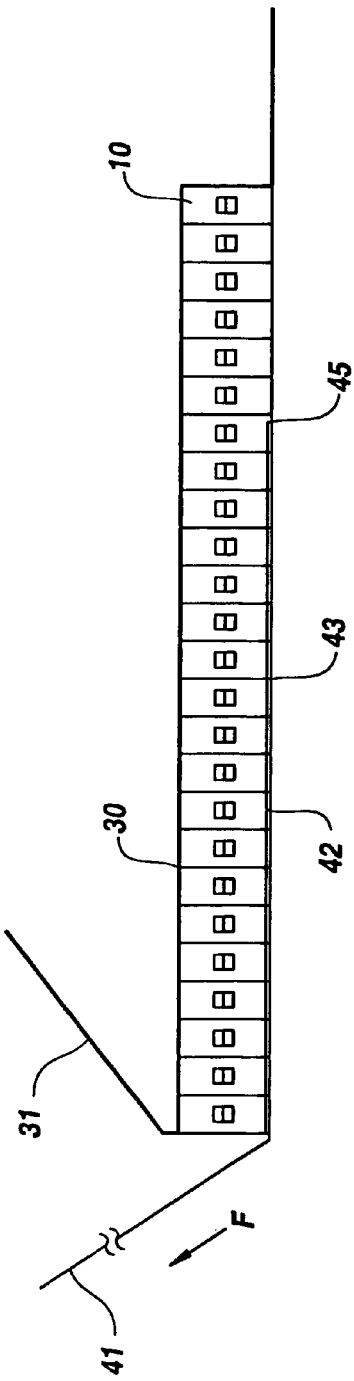

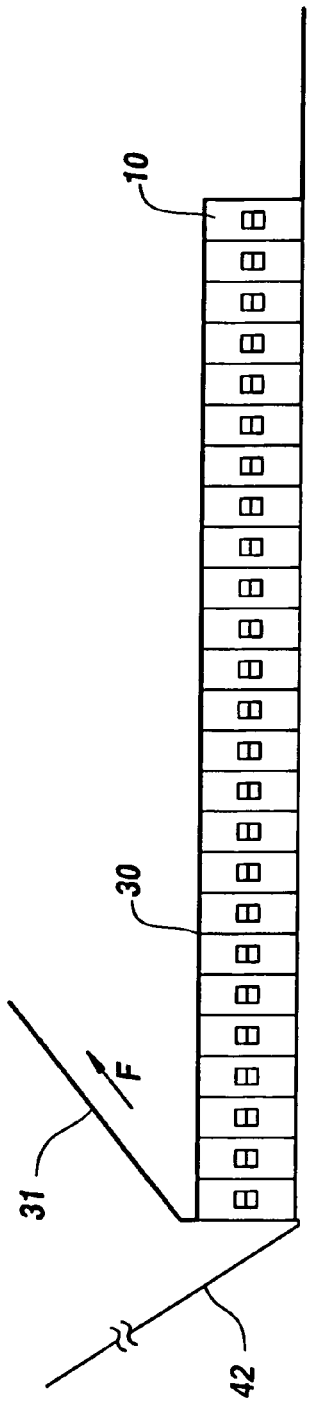
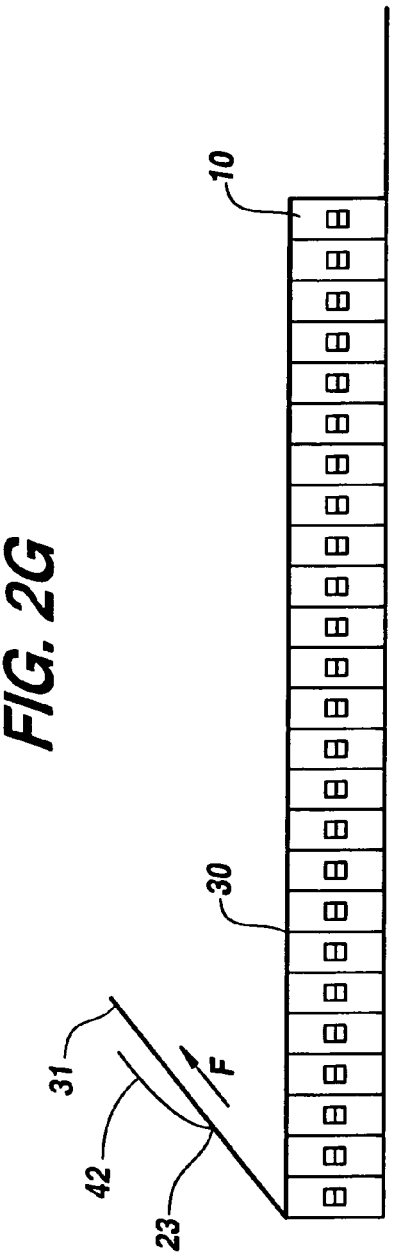

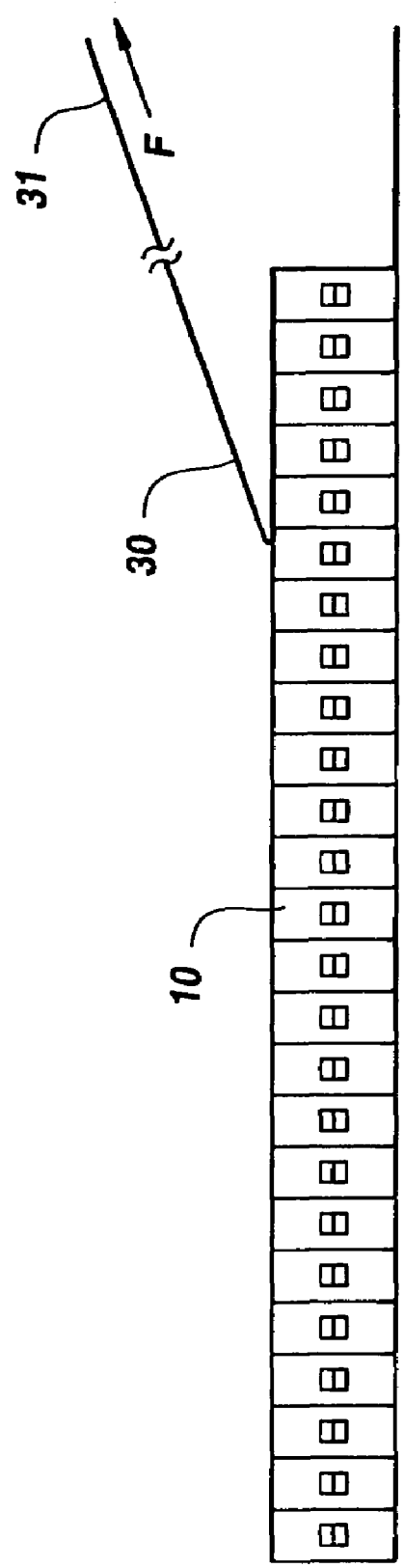

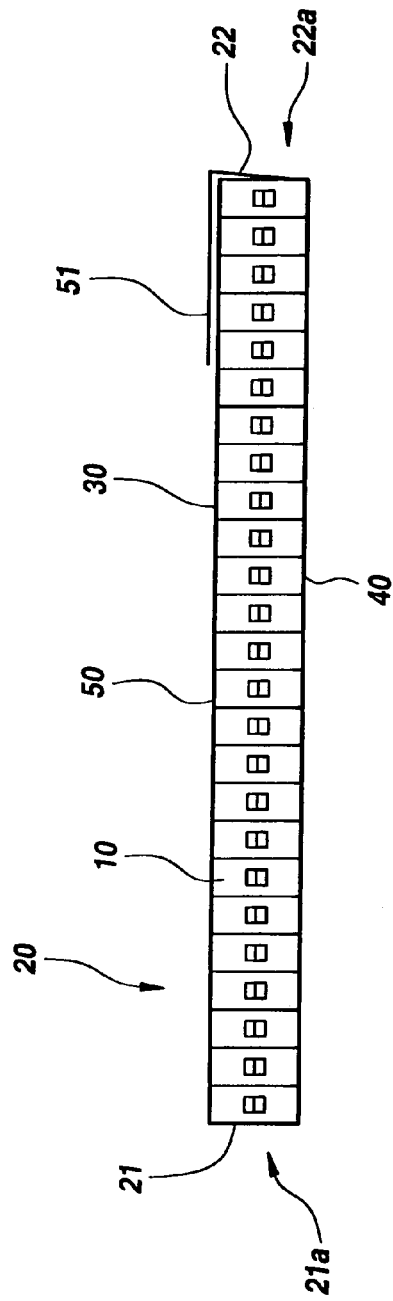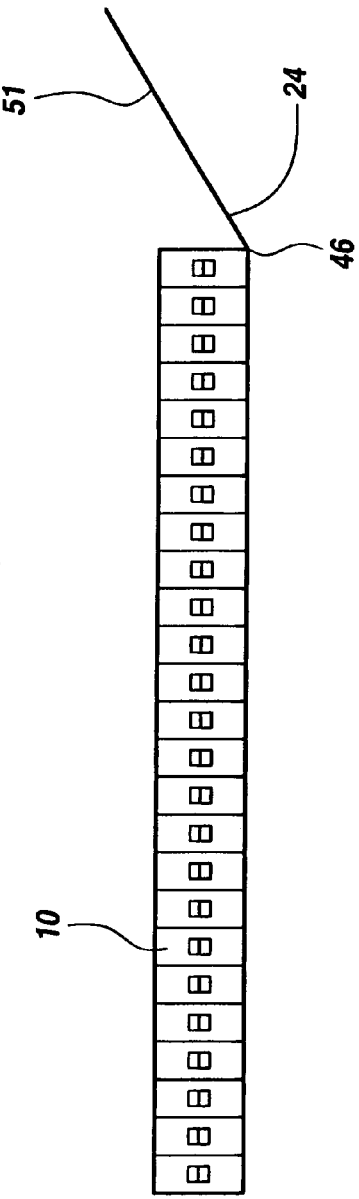

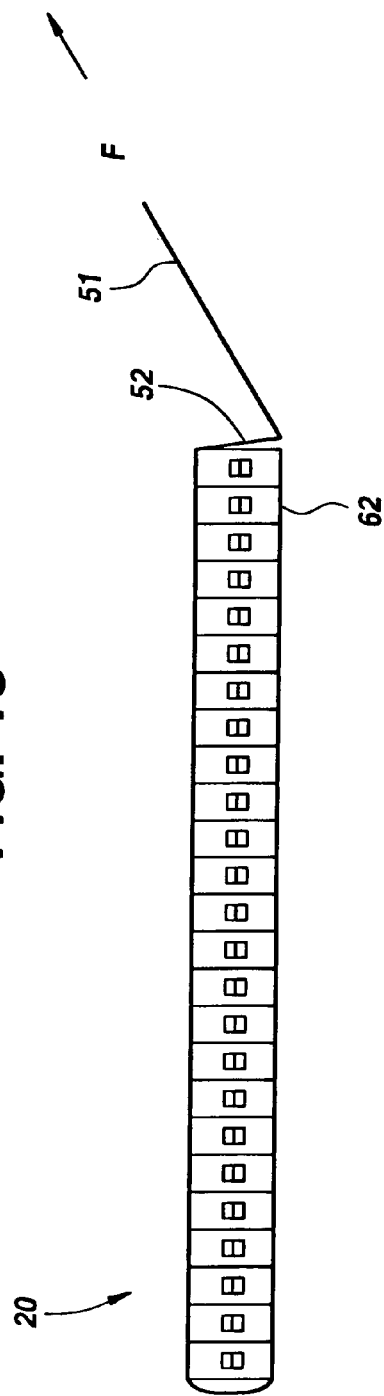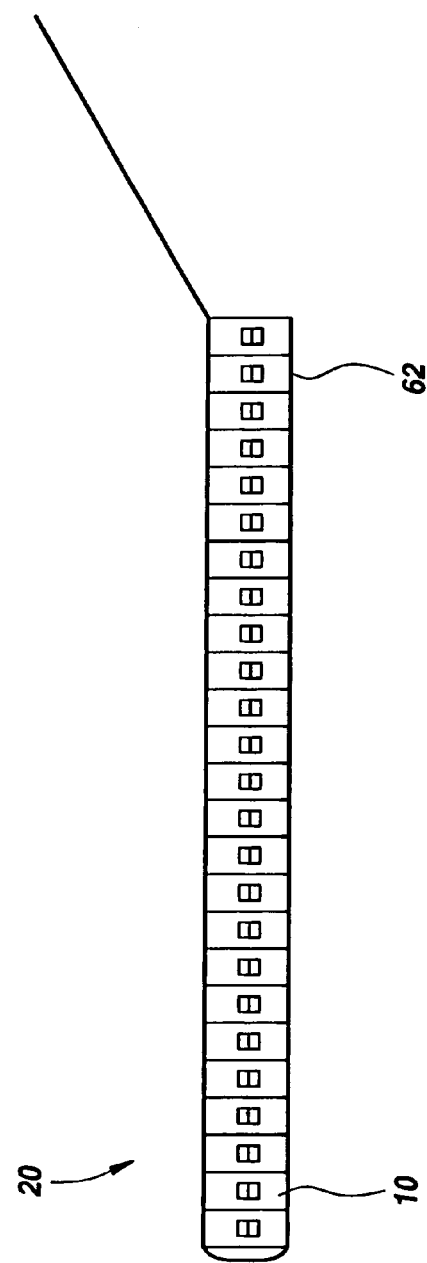

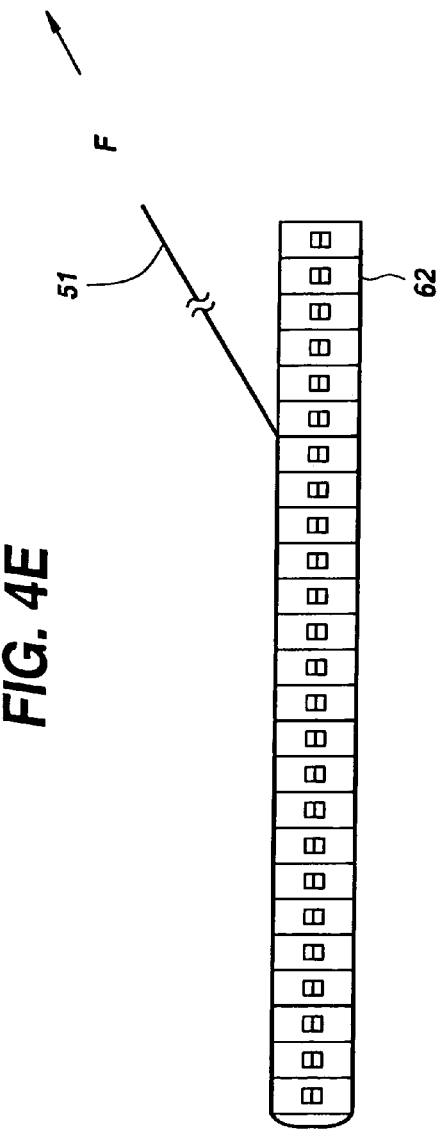
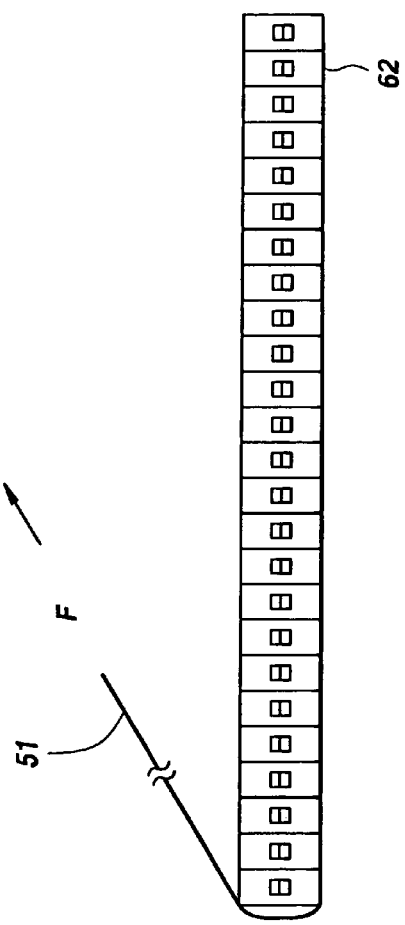

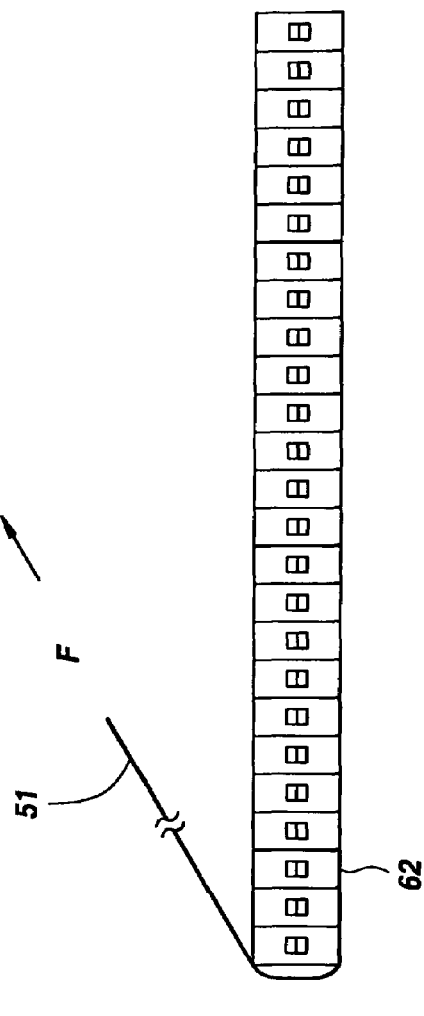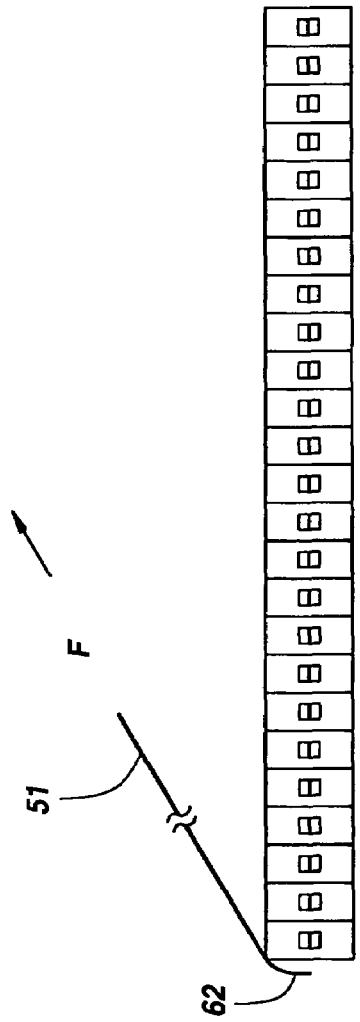

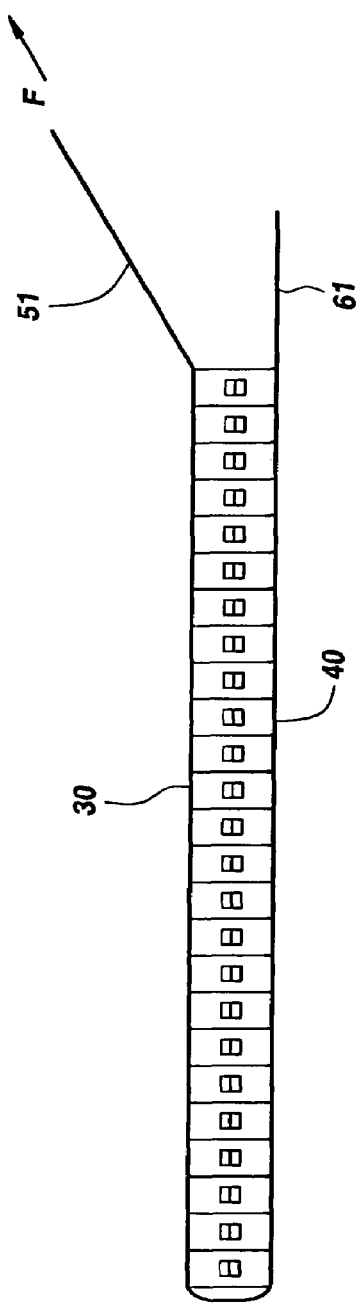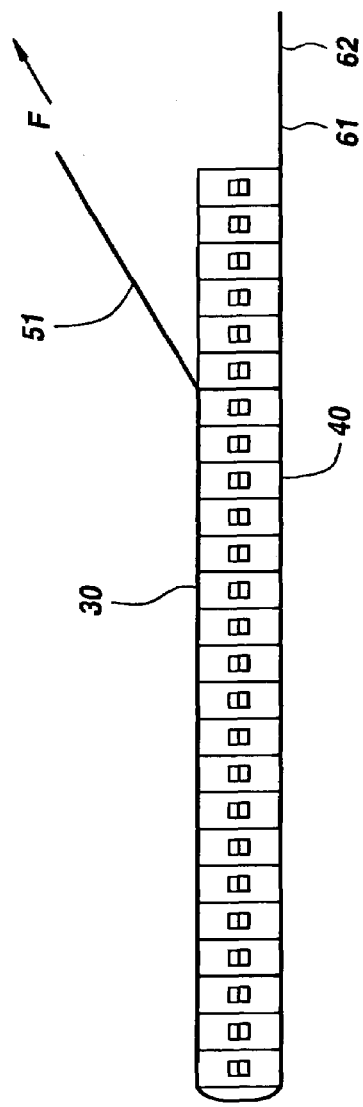

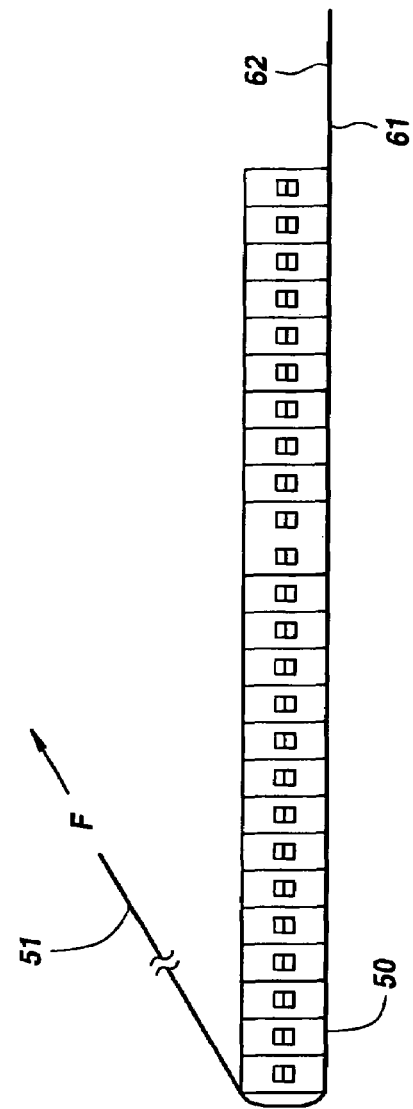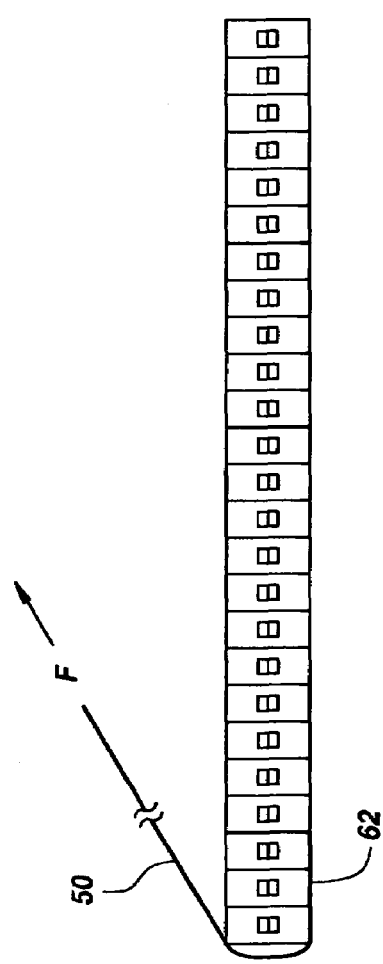
FIG. 5F
FIG. 5G

PACKAGING OF MULTIPLE FLUID RECEPTACLES

RELATED APPLICATIONS

The present application is a continuation-in-part of and claims priority to U.S. Ser. No. 10/684,536 filed on Oct. 14, 2003 now abandoned.

BACKGROUND OF THE INVENTION

1. Field of the Invention

The present invention relates to packaging of multiple fluid receptacles, in particular to packaging cuvettes used in a clinical analyzer and a method for inserting cuvettes into an analyzer.

2. Description of the Related Art

Receptacles, such as cuvettes for containing a liquid for analysis or handling, including those having multiple reservoirs, are known in the art as disclosed, for example, in U.S. patent application Publication No. 2003/0003591 A1, Des. 290,170 and U.S. Pat. No. 4,639,135. When cuvettes are used, the cuvettes should be free of contaminates for several reasons. First, when a chemical reaction occurs in the cuvette, the contaminates may taint or interfere with the chemical reaction. Second, particles may interfere with the addition, removal or mixing of fluids by partially or completely obstructing metering devices, such as aspirating nozzles, that could be used for performing such operations. Third, any foreign object in the light path of a measuring device, such as a photometer, may corrupt the measurement by partial obstruction or refraction of the available light. This includes particles within the fluid inside the cuvette, particles adhering to the outside of the cuvette over the read window, and smudges on the read windows, such as fingerprints. Finally, particles may scratch the cuvette read windows during transport. The scratch may then interfere with the photometric or spectrophotometric measurement.

It is known to load multiple cuvettes into an analyzer as disclosed in U.S. Pat. Nos. 4,636,477 and 6,328,164 and as shown in FIGS. 1a-c. The current method of bulk packaging, as shown in the '164 patent and in FIGS. 1a-c, is to fasten the tops of the cuvettes to a flexible support that is coated with an adhesive. As shown in FIG. 1a, cuvettes (10) are adhered to a plastic web (50) by adhesive. Upon insertion of the cuvettes and paper web support into an analyzer, the support is pulled away from the cuvettes leaving the individual cuvettes loaded into the analyzer. The cuvettes are oriented such that the read windows are stacked side by side to face one another. This facilitates some degree of protection to the read window as well as reducing the opportunity for particles to enter the cuvettes. The adhesive used must be strong enough to hold the cuvettes during handling but must cleanly release the cuvette following insertion into an instrument. Several problems with this packaging system includes the cuvettes prematurely separating from the support media (see FIG. 1b), the end cuvettes being unprotected from surface contamination, and the cuvettes not remaining in intimate contact with each other allowing particulates to get between the cuvettes. See FIG. 1c where the packaged cuvettes sag when held by the ends, forming gaps between individual cuvettes.

SUMMARY OF THE INVENTION

One object of the invention is to overcome the disadvantages of the known art described above. Another object of the invention is to provide packaged articles such as fluid receptacles, having an improved removable support for holding the articles together until they are used in order to prevent the articles from being detached before their intended use. Another object of the invention is to provide packaged cuvettes, such as those used in a clinical analyzer, that are packaged in a manner to reduce or prevent contamination of the read windows in the individual cuvettes, and that prevent the cuvettes from being detached before their use. Yet another object of the invention is to provide a method for inserting a plurality of cuvettes into a clinical analyzer in a manner which prevents or reduces the likelihood of the individual cuvettes becoming contaminated or separated.

The foregoing and further objects of the invention are accomplished according to one aspect of the invention that provides packaged fluid receptacles that include: a plurality of fluid receptacles arranged one next to the other to form a composite structure having a top surface, bottom surface and end walls at a first end and a second end and having a longitudinal axis which extends through the end walls; and a removable support which contacts at least the top surface, bottom surface and end walls, the removable support including an attachment for applying a force sufficient to remove the support, preferably in a direction along the longitudinal axis. In a preferred embodiment, the support is a web that has an adhesive on at least a portion of the web that contacts the top surface of the composite structure to anchor the individual fluid receptacles to the support. In another preferred embodiment, the web has a top and bottom portion, wherein the top portion contains the adhesive that contacts the top surface of the composite structure. In still another preferred embodiment, the top portion contacts the end walls of the composite structure and the top portion and bottom portion are joined at the bottom of the end walls at the first and second ends. Preferably, the bottom portion of the web contains no adhesive; and more preferably, the web further comprises a perforation in the vicinity of the joining of the top and bottom portion at the second end to provide for separation of the top and bottom portion upon application of the force.

According to another preferred embodiment, at least a portion of the bottom portion of the web has an adhesive to contact the bottom surface of the composite structure, and the bottom portion is divided into a first portion which extends from the first end to the second end and a second portion that doubles back on the first portion from the second end back to the first end, and wherein the adhesive is located on the first portion.

According to yet another preferred embodiment, the removable support, preferably a web, is one-piece and the web includes a top and bottom portion, wherein the top portion contains the adhesive that contacts the top surface of the composite structure, the top portion of the web has a first end located in the vicinity of the second end wall and the bottom portion of the web has a second end located in the vicinity of the second end wall, and the attachment is located at the first end of the web.

Preferably, the fluid receptacles are cuvettes usable in a clinical analyzer.

Another aspect provides packaged cuvettes for use in a clinical analyzer that includes, a plurality of cuvettes having windows for measuring an aspect of the contents of the cuvettes and arranged such that the windows face each other to form a composite structure having a top surface, bottom surface and end walls at a first end and a second end; and a removable supporting web which contacts at least the top surface, bottom surface and end walls. In a preferred embodiment, the supporting web includes a tab capable of being pulled by hand located in the vicinity of the first end for applying a force to remove the web upon application of a sufficient force, preferably in a lengthwise direction relative to the web. In another preferred embodiment, the supporting web includes a tab capable of being pulled by hand located in the vicinity of the second end for applying a force to remove the web.

Yet another aspect of the invention provides a method for inserting a plurality of cuvettes into a clinical analyzer that includes: providing packaged cuvettes as described above; inserting the packaged cuvettes into a cuvette loading station of a clinical analyzer in a manner in which the tab remains accessible to application of a force; securing the packaged cuvettes in the loading station; applying a force to the tab in a direction toward the first end to peel back the support from the cuvettes; and removing the support to provide individual cuvettes.

Still another aspect of the invention provides a method for inserting a plurality of cuvettes into a clinical analyzer that includes: providing the packaged cuvettes having the tab located in the vicinity of the second end; inserting the packaged cuvettes into a cuvette loading station of a clinical analyzer in a manner in which the tab remains accessible to application of a force; securing the packaged cuvettes in the loading station; applying a force to the tab to peel back the support from the cuvettes; and removing the support to provide individual cuvettes.

Further objects, features and advantages of the present invention will be apparent to those skilled in the art from detailed consideration of the preferred embodiments that follow.

BRIEF DESCRIPTION OF THE DRAWINGS

FIGS. 2a-h show a schematic side view of packaged cuvettes and the removal of the packaging according to one embodiment of the present invention.

FIGS. 4a-i show a schematic side view of packaged cuvettes and the removal of the packaging according to another embodiment of the present invention.

FIGS. 5a-i show a schematic side view of packaged cuvettes and the removal of the packaging according to another embodiment of the present invention.

DETAILED DESCRIPTION OF PREFERRED EMBODIMENTS

Figure 1A:
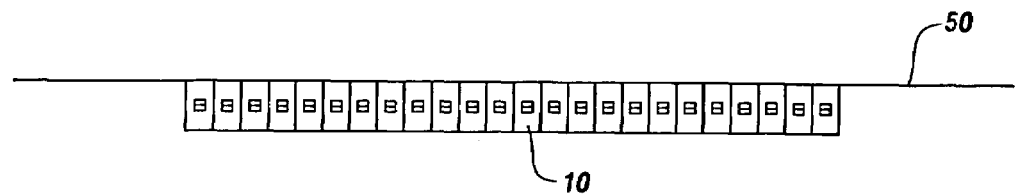
FIGS. 1a-c show a schematic side view of conventional packaged cuvettes.
Figure 1B:
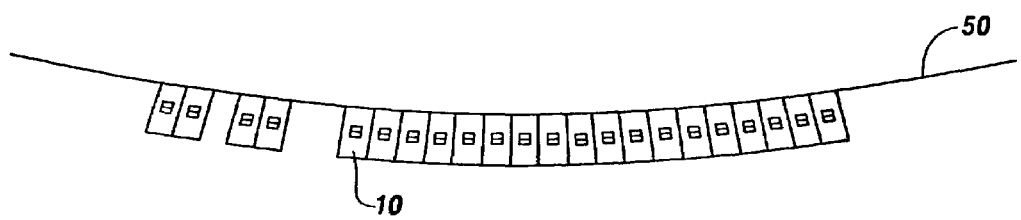
Figure 1C:
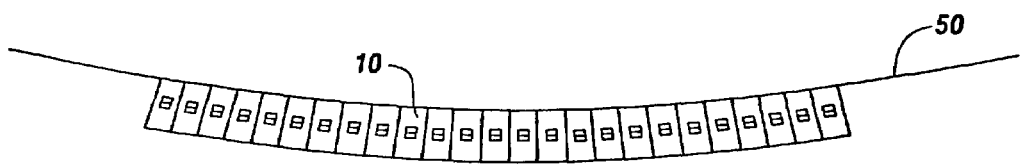

The present invention is directed to the packaging of articles, such as fluid receptacles, preferably cuvettes, in a manner that provides for effectively binding the articles together before use. This is accomplished by a removable support that surrounds the entirety of the packaged plurality of receptacles, i.e., the top and bottom surfaces and end walls of the composite structure formed by the packaged receptacles. Compared to the conventional art as described in conjunction with FIGS. 1a-c, the present invention provides the following benefits, particularly when the receptacles are cuvettes:

1) The end cuvette read windows are protected from contamination.
2) The cuvettes are held together preventing particles from entering between cuvettes.
3) The stack is held rigidly preventing cuvettes from separating from the top support prior to the removal of the bottom support.
4) Having all of the cuvettes more rigidly aligned to each other enhances cuvette loading in the instrument in which the cuvettes will be used, particularly in clinical analyzers.

The present invention results in improvements in ease of handling and provides a higher degree of confidence that the integrity of the fluid receptacles, preferably cuvettes, has been maintained.

Another important feature of the present invention is that the support which holds the fluid receptacles together can be removed relatively easily when desired. In a preferred embodiment, when the fluid receptacles are cuvettes, the present invention provides an improvement in the ease of use in handling and loading of the cuvettes used for clinical analyzers while providing additional protection from contamination. This is a significant improvement to conventionally packaged cuvettes in that it abates the opportunity for the introduction of particulates on the cuvettes as well as contamination of the optical read windows.

The present invention solves the above problems and provides the above advantages by providing a plurality of articles arranged one next to the other to form a composite or integral structure. The articles can be anything capable of being arranged together, such as receptacles for receiving a fluid. Of course, fluid receptacles that have surfaces complimentary to each other, such as flat or planar surfaces, that will fit together in an orderly fashion, such as polygons are preferred. Particularly preferred are cuvettes for clinical analyzers, such as shown in FIGS. 1-5 as reference numeral 10. Other examples of cuvettes usable in the present inventions are shown in U.S. patent application Publication No. 2003/0003591 A1 and U.S. Pat. No. 4,690,900, both of which are incorporated herein by reference in their entireties. Preferred cuvettes are those having multiple reservoirs and windows. When cuvettes are used, they are preferably arranged together with the windows facing one another to prevent or reduce the contamination described above.

The composite structure formed by the fluid receptacle will have a top surface, bottom surface and end walls. The end walls are located at a first end and a second end. A longitudinal axis is formed that extends through the end walls of the composite article. Surrounding the composite structure is a removable support that contacts the top surface, bottom surface and end walls. The removable support acts to bind the individual fluid receptacles together to form the integral composite structure. The removable support includes an attachment for applying a force that removes the support upon application of a sufficient force in a direction of the longitudinal axis leaving the individual articles ready for use.

The removable support can be any structure capable of holding the individual fluid receptacles together. Preferably, the removable support is a paper or plastic web that acts to band the fluid receptacles together. Other supports could include a cord, rope, band or the like. As described more fully below in connection with the preferred embodiments, the supports can be a single unitary piece that completely surrounds the composite structure, or the support can be multiple pieces, for example, two webs, one of which extends along the top surface of the composite structure and the other of which extends along the bottom surface of the composite structure.

In a preferred embodiment, the removable support is anchored or joined to the composite structure by an adhesive, which preferably contacts the top surface of the composite structure. In other embodiments, the support can anchor the articles by application of adhesive at the top and bottom surfaces and even the end walls of the composite structure.

The attachment for applying a force can be anything capable of applying a force to the removable support. For example, the attachment can be an extension of the removable support that does not actually surround the composite structure. If the support is a two-part support, each part of the support can have an extension that extends from the support to form the attachment. See, e.g., FIG. 2b for upper and lower tabs. Alternatively, the attachment can be a different structure than the support, e.g., a plastic or metal tab adhered to a paper web support.

As noted above, the support is removable upon the application of a sufficient force to the attachment. The support, therefore, is preferably separable from itself at some point along the support. For example, when the support is a web, a perforation may be provided, preferably a distance away from the attachment for applying a force. Upon application of the force, the web will tear at the perforation causing the web to separate from itself. The web can also be separated by providing a two-piece web and joining the webs together with a removable pressure-sensitive adhesive, again preferably at a distance way from the attachment. Upon application of the force, the two webs will separate from each other at the point where they are joined by adhesive, thus enabling simplified removal of the support.

In another embodiment, the web is also in two parts. The top portion of the web contacts the end walls of the composite structure and the top portion and bottom portion of the web are joined at the bottom of the end walls at the first and second ends. In this embodiment, at least a portion of the bottom portion of the web has an adhesive which contacts the bottom surface of the composite structure to hold the web to the bottom surface.

In this embodiment, the bottom portion is divided into a first portion having the adhesive and a second portion. The first portion extends from the first end to the second end and the second portion doubles back on the first portion from the second end back to the first end. The second portion ends at the first end or beyond to form the integral attachment. Upon application of a force to the end of the second portion, the second portion acts to pull the first portion containing the adhesive away from the composite structure in a direction toward the first end.

In a particularly preferred embodiment, a design is provided that provides the same advantages of protecting the receptacles from premature release and contamination, and also includes the added advantage of a simplified design and ease of use. In certain embodiments, such as those described above, an attachment may be at both ends of the receptacle stack to facilitate handling and loading. In those embodiments where the receptacles are cuvettes, insertion of the cuvette stack into the analyzer may require two hands and removal of the packaging material may require two hands. In the preferred embodiment, the attachment is at one end of the stack only, allowing single-handed insertion and package removal, or at least single-handed insertion and two-handed removal of the removable support. Even in the two-handed removal, advantages are found in that both hands are at the front of the analyzer for removal of the support because the attachment is at the rear end. In contrast, in some other embodiments, reaching into the analyzer is required. Furthermore, automated application of the removable support is easier in this embodiment than in the prior art or other embodiments because a continuous ribbon of material may be used to package the receptacles.

In this embodiment, the removable support is preferably in one-piece. The top portion of the support has an adhesive which contacts the top surface of the composite structure. The support extends along the first end, the bottom surface and second end. The one piece support thus wraps around the composite structure. The ends of the support are attached, such as by a thin strip of adhesive, in the vicinity of the second end, preferably at the base of the second end. A perforation can be provided to provide for easier separation when the removable support is removed. At least one end of the support, preferably that portion of the support that extends along the top surface of the composite structure includes an attachment, such as a tab that can extend from the packaged receptacle.

To remove the removable support, the attachment is pulled in a direction away from the second end to tear the perforation or otherwise separate the two ends of the support. Continued pulling of the attachment in an upward direction will result in the adhesive portion of the support separating and releasing the top surfaces of the individual fluid receptacles. After the adhesive portion of the support is separated from the top surface of the composite article the non-adhesive support along the bottom surface of the composite article is then pulled away from the bottom surface in a direction toward the first end of the composite article, such as shown in the embodiment of FIGS. 4g and 4h. In a preferred embodiment where the fluid receptacles are cuvettes, the first end is inserted into the track of a cuvette feed station of a clinical analyzer. The attachment or tab can then be pulled by an operator to remove the support without the necessity of contacting the first end that has been inserted into the analyzer.

Another preferred embodiment, such as described in connection with FIG. 5 is similar to that described above. In this embodiment, however, each end of the support has an extension, which can extend away from the first end of the packaged receptacle. The extension, such as tabs, are bonded together. To remove the support, the extensions are separated from one another. The extension that is part of the support which extends along the top surface of the packaged receptacles is pulled in a direction which results in the adhesive surface of the support separating from the individual receptacles. The remainder of the support is separated from the packaged receptacles in the same manner as described above.

In a preferred embodiment, the clinical analyzer that receives the cuvettes will have rails upon which the cuvettes rest to form a track. The portion of the support that runs underneath the cuvettes must be no wider than the width between the two rails to prevent interference between the rails and that portion of the support that runs underneath the cuvettes.

Now reference will be made to the non-limiting preferred embodiments shown in the FIGS. 2-5.

Figure 2A:
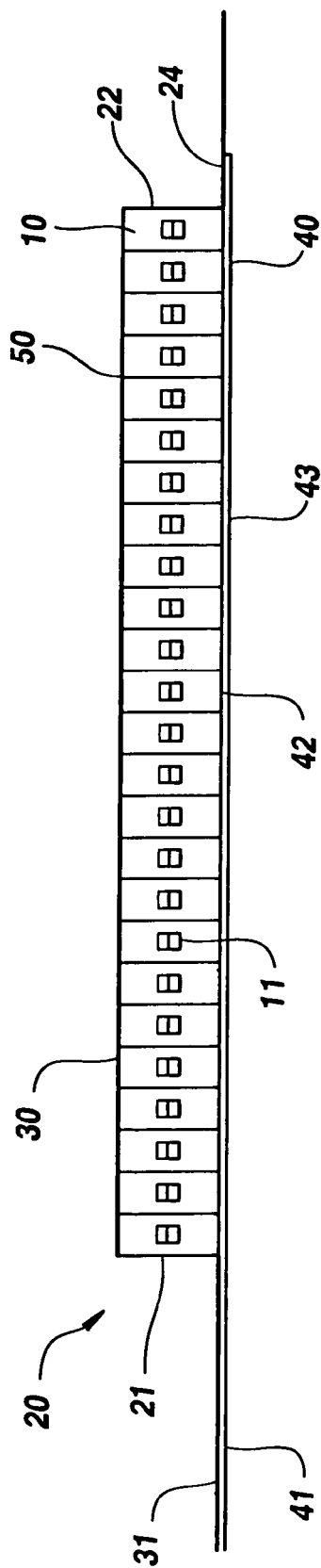
Figure 3A:
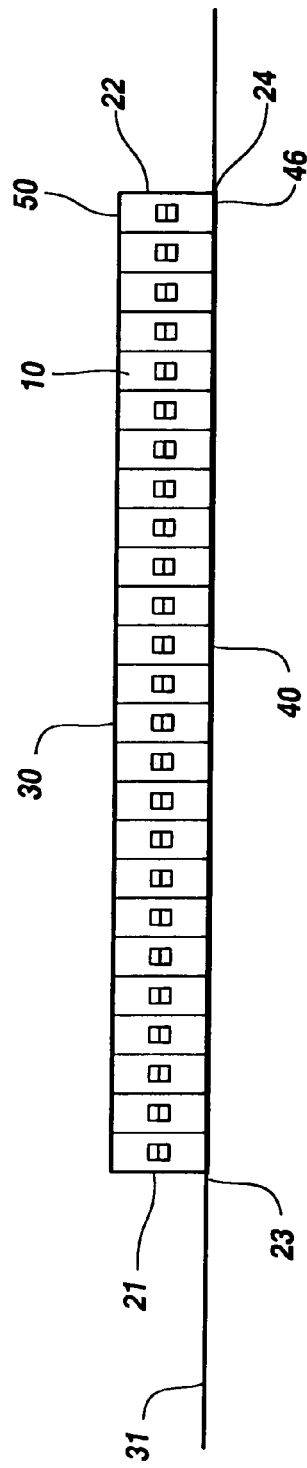
FIGS. 3a-e show a schematic side view of packaged cuvettes and the removal of the packaging according to another embodiment of the present invention.
Figure 3B:
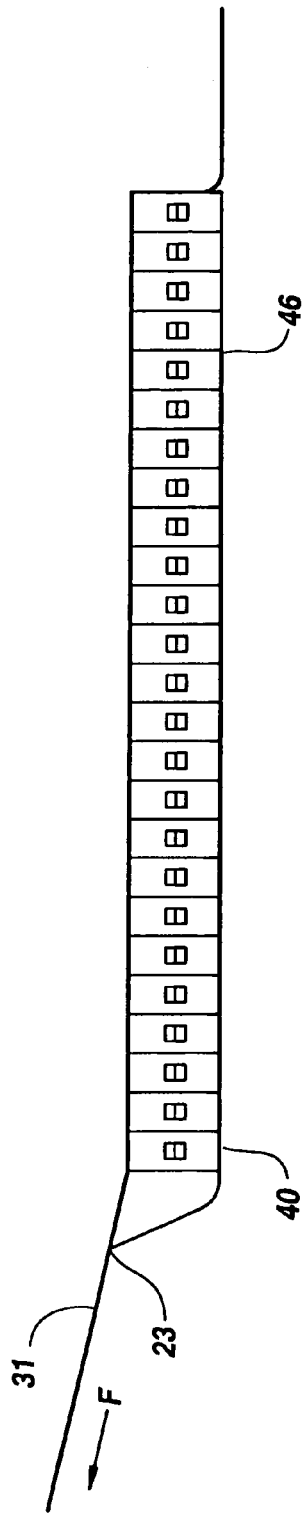
Figure 3C:
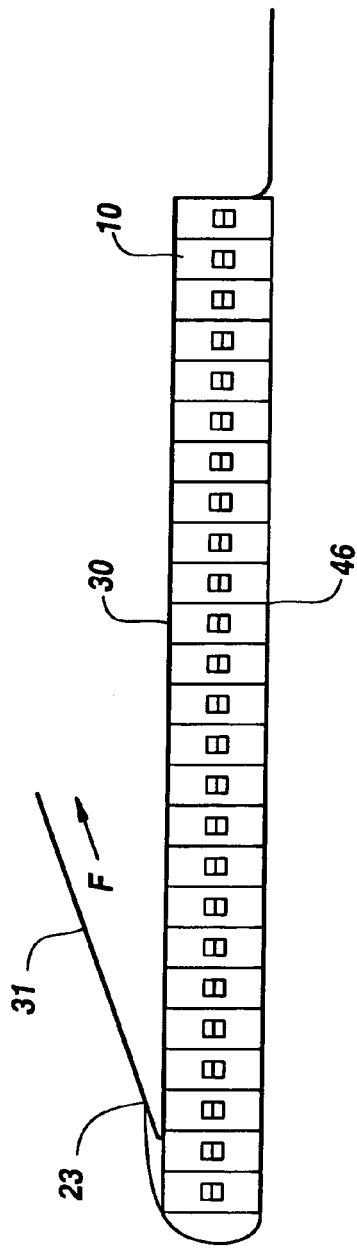
Figure 3D:
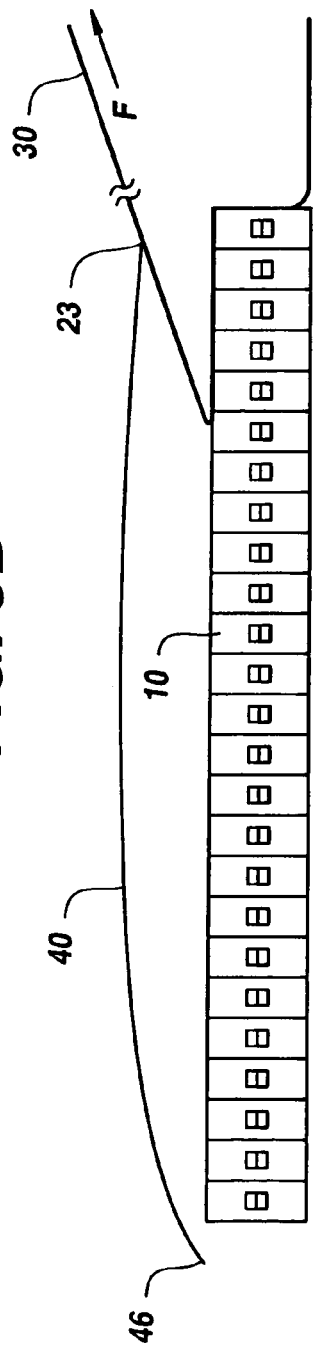
Figure 3E:
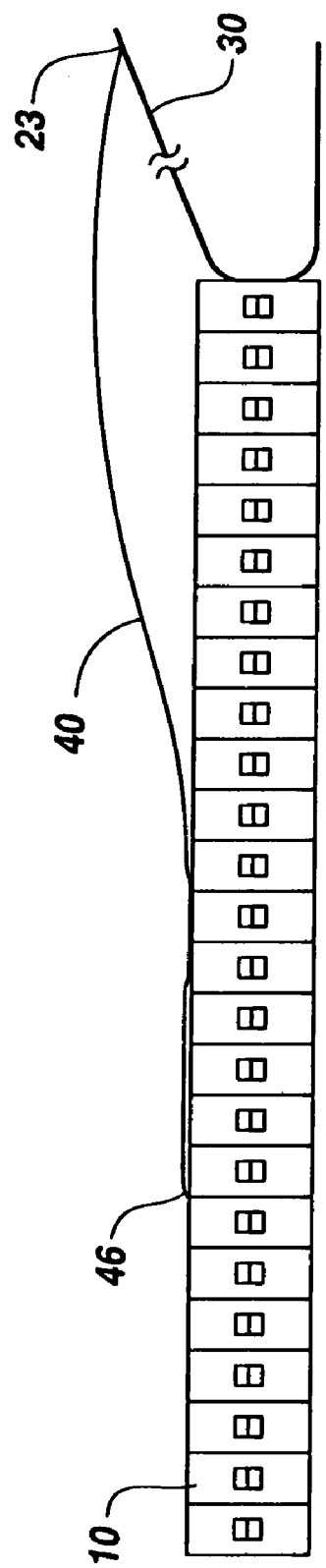

In the embodiment shown in FIG. 2, a composite structure (20) of 25 individual cuvettes (10) is shown surrounded by a removable support (50). In this embodiment, the removable support is a two-part web. The top portion of the web (30) as shown in FIG. 2a extends over the top surface of the composite structure and down along the first (21) and second (22) end walls of the composite structure. The top portion of the web includes an extension or tab (31) which extends away from the first end wall (21). The extension (31) along with extension (41) (described below) are capable of having a force applied thereto.

The bottom portion (40) extends along the bottom surface of the composite structure (20) in two lengths or portions. A first portion (42) (see FIG. 2a) of the bottom portion (40) runs from the first end wall to the second end wall. An adhesive (not shown) is applied to at least a part of the first portion (42) to join the bottom portion of the web to the bottom surfaces of the composite structure. The adhesive can be applied to the entirety or just a portion of the first portion (42) of the bottom portion (40). A second portion (43) doubles back under the first portion (42) in a direction toward the first end wall (21). The second portion can be a separate piece of web that attaches to the first portion in the vicinity of end wall (22), or alternatively, the first and second portion can be a single piece. The second portion generally will not include any adhesive applied to it.

The second portion (43) of the bottom portion (42) of the web also includes an extension or tab (41) which extends away from the first end wall (21) and co-extends with extension (31). As noted above, both extensions are capable of having a force applied thereto.

In the present embodiment, the top and bottom portions (through first portion (42)) of the web are connected to one another at the bottom of each end wall (21) and (22). Specifically, the top and bottom portions can be connected by adhesive at regions (23) and (24).

As shown in FIG. 2a, the packaged cuvettes are ready to be inserted into a clinical analyzer for individual use. The packaged cuvettes can be loaded into an analyzer, for example, into a loading station having rails for holding the cuvettes when the cuvettes have been separated from one another upon removal of the removable support. The rails support the cuvettes from the bottom. The removable support, at least along the bottom surface of the packaged cuvettes, has a width that does not extend to the edges of the cuvettes and thus does not interfere with the rails. In this embodiment, the cuvettes have extensions or hooks (11) that extend away from the cuvettes and are grasped within the analyzer for transport and manipulation of the cuvettes within the analyzer. The packaged cuvettes can be inserted either end into the analyzer depending upon the configuration of the analyzer. A stop or one-way gate is provided on the analyzer, which prevents the cuvettes from easily coming out of the loading station in the same direction they were loaded into the analyzer. The stop can be similar to those describe in U.S. Pat. No. 6,328,164, which is incorporated herein by reference in its entirety.

The description of FIGS. 2b to 2h, describes the packaged cuvettes already loaded into the analyzer. For purposes of clarity, the analyzer is not shown in FIGS. 2b to 2h.

In FIGS. 2b and 2c, the beginning of the removal of the removable support is depicted. Specifically, the tabs or extensions (31) and (41) are separated so that force can be applied only the lower tab (41) in the direction (F). Upon application of a sufficient force, the bottom portion (40) is separated from the top portion (30) at securing region (24). Following separation of the bottom part from the top part, the second portion (43) pulls (peels) first portion (42) away from the bottom of packaged cuvettes (20). FIG. 2d shows the first portion (42) just beginning to pull away from the bottom of composite structure (20) at region (44). FIG. 2e shows the first portion pulling away from the bottom of composite structure at region (45).

FIG. 2f shows the bottom of the composite structure completely free of the removable support. When the first portion (42) of the bottom portion is completely pulled away from the composite structure, region (23), where the top portion (30) is connected to the bottom portion (40) is reached. At this point the force (F) can continue to be applied to bottom portion (through first portion (42)). More preferably, the force is now applied to tab (31). Further application of force to either first portion (42) or tab (31) causes the bottom portion (40) to begin pulling the top portion (30) away from first end wall (21) as shown in FIG. 2g. Further application of force causes the first section to pull away from the top of the composite article as shown in FIG. 2h until the removable support is completely pulled away from the composite structure leaving the individual cuvettes ready for use.

FIG. 3 shows an alternative embodiment for the removable support (50). In this embodiment, the top portion of the web (30) extends over the top surface of the composite structure (20) and is adhesively anchored or joined to the top surface of the composite structure as shown in FIG. 3a. The top portion of the web also includes an extension or tab (31) capable of having a force applied to it. The web also includes a bottom portion (40) that extends underneath the composite structure (20). However, unlike the embodiment shown in FIG. 2, there is no doubling back of the bottom portion from the second end wall (22) to the first end wall (21). Instead, bottom portion (40) is connected (preferably by adhesive) to the top portion (30) at the bottom of first end wall (21) in the region (23) and at second end wall (22) in the region (24) as shown in FIG. 3a. A perforation (46) or some other weakening is supplied in the region of end wall (22).

Upon application of a force (F) to tab or extension (31), a tension is applied to bottom portion (40) by virtue of the connection of top portion (30) and bottom portion (40) through region (23). The resulting tension or force causes the bottom portion (40) to separate from top portion (30) in the region of second end wall (22) at perforation (46). See FIG. 3b. It is also important to note, however, that perforation (46) does not necessarily have to be provided. For example, it would also be possible to detach bottom portion (40) from top portion (30) by simply pulling the portions apart at region (24). Further application of force (F) to tab (31) in a direction toward second end wall (22) (FIG. 3c) causes the bottom portion to separate from the bottom surface of the composite structure, while at the same time causing the top portion to pull away (or peel back) from the top surface of the composite structure.

Upon application of a sufficient force, the bottom portion (40) is pulled completely away from the bottom surface of composite structure and across the top surface of the composite structure. At the same time, the top portion (30) is completely peeled away from the top of the composite structure. See FIGS. 3d and 3e. Continued application of force will remove the top portion (30) from the end wall (22) leaving individual cuvettes ready for use.

In the embodiment of FIG. 4, the extension (51) of the removable support is located at the second end (22a) of the packaged cuvettes. Specifically, in the embodiment shown in FIG. 4, a composite structure (20) of 25 individual cuvettes (10) is shown surrounded by a removable support (50). In this embodiment, the removable support is a one-piece web. The web has a first end (52) and second end (62) as shown in FIG. 4c. In this embodiment, only the top portion of the web has adhesive. The top portion as shown in FIG. 4a extends over the top surface of the composite structure and down along the first (21) and second (22) end walls of the composite structure to adhesively secure the tops of the individual cuvettes (10). The top portion of the web includes an extension or tab (51) which extends away from the second end wall (22). As shown in FIG. 4a the extension (51) is folded back onto the top portion of the web (30) until the packaged cuvettes are ready for insertion into a clinical analyzer. The extension (51) is capable of having a force applied thereto.

The bottom portion (40) of the one-piece web extends along the bottom surface of the composite structure (20) and is not adhesively attached to the bottom surface of the composite structure.

In the present embodiment, the top and bottom portions of the one-piece web have their ends (52, 62) connected to one another in the region of second end wall (22), preferably at the bottom of end wall (22). Specifically, the ends of top and bottom portions can be connected by adhesive at region (24) as shown in FIG. 4b.

As shown in FIG. 4a, the packaged cuvettes are ready to be inserted into a clinical analyzer for individual use as described in connection with FIG. 2. The packaged cuvettes can be inserted first end (21a) first into the analyzer. As noted above, this allows the operator to remove the web by manipulating the tab (51) at only a single end (22a) of the packaged cuvettes. A stop or one-way gate is provided on the analyzer, which prevents the cuvettes from easily coming out of the loading station in the same direction they were loaded into the analyzer. The stop can be similar to those describe in U.S. Pat. No. 6,328,164.

The description of FIGS. 4b to 4i, describes the packaged cuvettes already loaded into the analyzer. For purposes of clarity, the analyzer is not shown in FIGS. 4b to 4i.

Figure 4I:
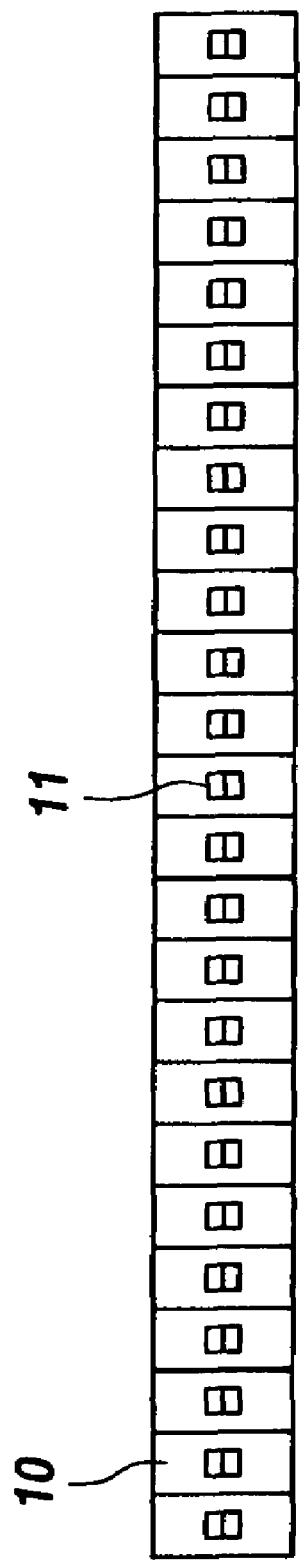

In FIG. 4b, the beginning of the removal of the removable support is depicted. Specifically, the tab or extension (51) is unfolded from the packaged cuvettes so that force can be applied to tab (51) in the direction (F). Upon application of a sufficient force, the bottom portion (40) is separated from the top portion (30) at securing region (24) by tearing perforation (46) as shown in FIG. 4c. Following separation of the bottom part from the top part, the top portion (30) pulls (peels) away from the top of packaged cuvettes (20) by continued application of force (F). FIGS. 4d-4e show the top portion (30) peeling away from the top of the composite structure. FIG. 4f shows the top portion of web completely separated from top of the composite structure. At this point, continued application of force (F) in a direction toward the second end pulls away the non-adhesive bottom portion of web (40) from the bottom of composite structure (20) in a direction from second end (22a) toward first end (21a) as shown in FIGS. 4f and 4g. That is, second end (62) of the web moves from second end (22a) of the composite structure to first end (21a). FIG. 4h shows the composite structure completely free of the removable support. FIG. 4i shows the removable support is completely pulled away from the composite structure leaving the individual cuvettes ready for use. The removable support can be discarded or recycled.

The embodiment shown in FIG. 5, is substantially identical to that shown in FIG. 4. The significant difference is that the bottom portion of the web (30) also includes an extension (61) which extends in the same direction as extension (51). The extensions can be adhesively joined together and folded onto the top of the composite structure in the same manner as the FIG. 4 embodiment. See FIG. 5c. When the cuvettes are ready for use, the tabs (61) and (51) are unfolded from packaged cuvettes as shown in FIG. 5b.

Figure 5A:
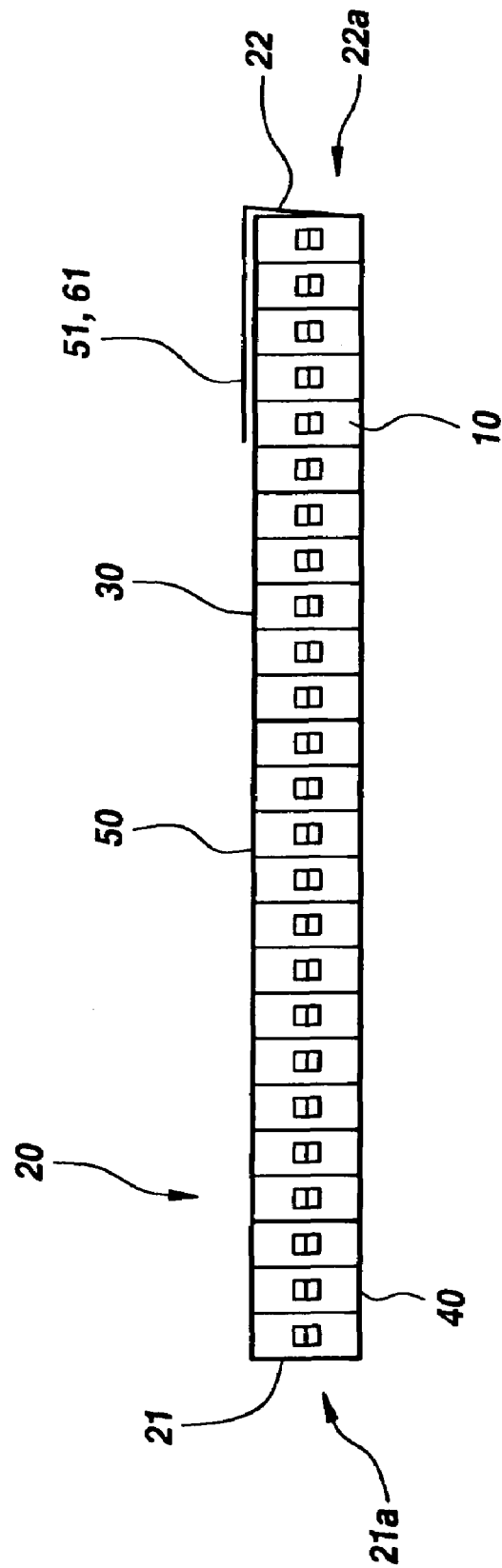
Figure 5B:
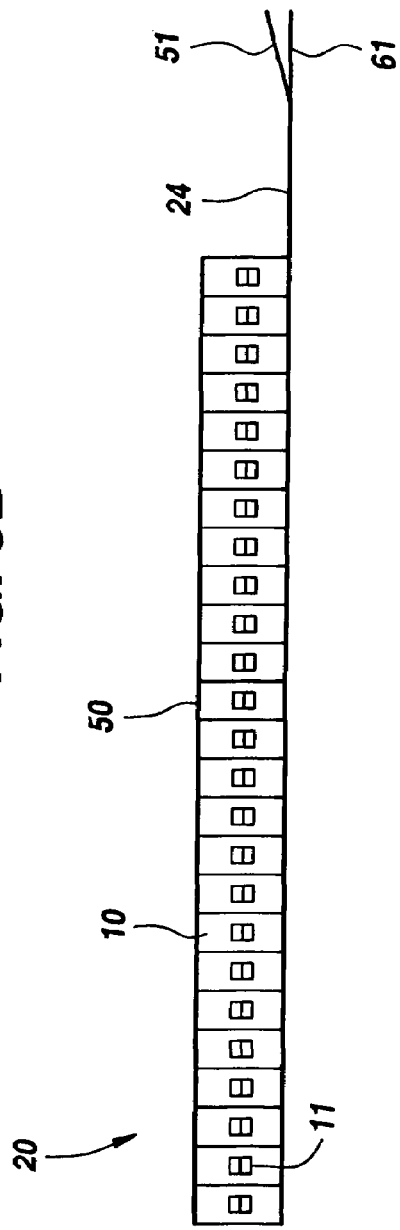
Figure 5C:
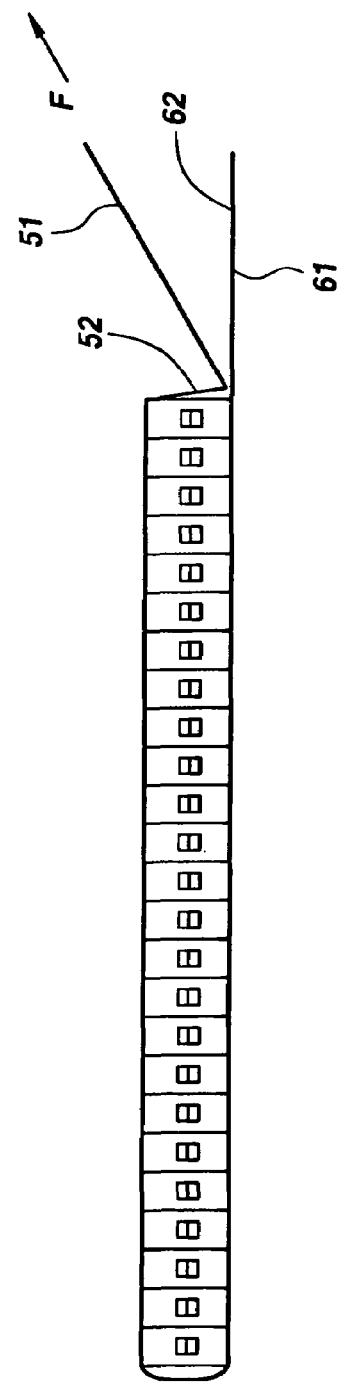
Figure 5H:
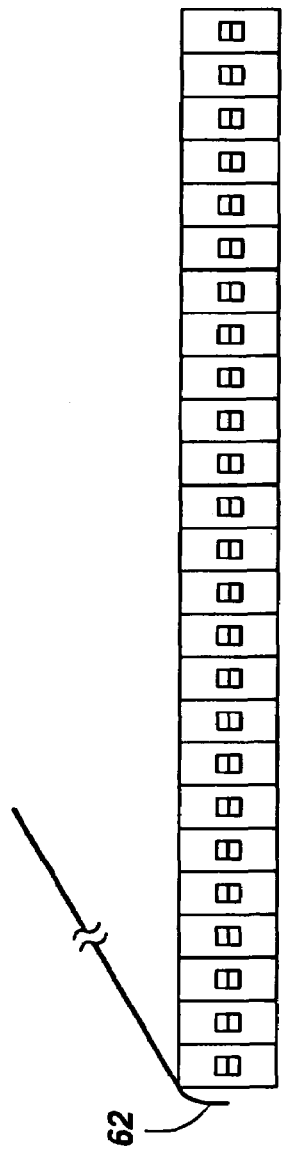
Figure 5I:
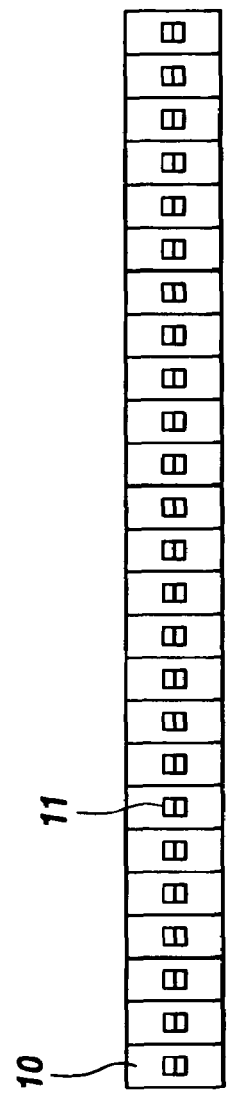

The tabs (61) and (51) are separated as shown in FIG. 5c and the web is then removed from the packaged cuvettes in the same manner as FIG. 4.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. Packaged fluid receptacles comprising:
   a plurality of fluid receptacles arranged one next to the other to form a composite structure having a top surface, bottom surface and end walls at a first end and a second end and having a longitudinal axis which extends through the end walls; and
   a removable support which contacts at least the top surface, bottom surface and end walls, the removable support including an attachment for applying a force in a direction along the longitudinal axis, wherein the removable support comprises a web having adhesive on at least a portion of the web that contacts the top surface of the composite structure to anchor the individual fluid receptacles to the support,
   wherein the web comprises a top portion and a bottom portion, wherein the top portion contains the adhesive that contacts the top surface of the composite structure,
   wherein the top portion contacts the end walls of the composite structure and the top portion and the bottom portion are joined at the bottom of the end walls at the first and second ends,
   wherein the bottom portion of the web contains no adhesive, and
   wherein the web further comprises a perforation in the vicinity of the joining of the top portion and the bottom portion at the second end to provide for separation of the top portion and the bottom portion upon application of the force.

2. Packaged fluid receptacles according to claim 1, wherein the web is paper or a plastic film.

3. Packaged fluid receptacles according to claim 1, wherein the attachment is located in the vicinity of the first end.

4. Packaged fluid receptacles as claimed in claim 1, wherein the attachment is a tab capable of being pulled by hand.

5. Packaged fluid receptacles as claimed in claim 1, wherein the attachment is a portion of the web that extends beyond the first end.

6. Packaged cuvettes for use in a clinical analyzer comprising:
   a plurality of cuvettes having windows for measuring an aspect of the contents of the cuvettes and arranged such that the windows face each other to form a composite structure having a top surface, bottom surface and end walls at a first end and a second end; and
   a removable supporting web which contacts at least the top surface, bottom surface and end walls, the supporting web including a tab capable of being pulled by hand located in the vicinity of the first end for applying a force in a lengthwise direction relative to the web to remove the web upon application of a sufficient force, wherein the removable supporting web has adhesive on at least a portion of the web that contacts the top surface of the composite structure to anchor the individual cuvettes to the support, wherein the supporting web further comprises a top portion and a bottom portion, wherein the top portion contains the adhesive that contacts the top surface of the composite structure, wherein the top portion contacts the end walls of the composite structure and the top portion and the bottom portion are joined at the bottom of the end walls at the first and second ends, wherein the bottom portion of the web contains no adhesive, and wherein the supporting web further comprises a perforation in the vicinity of the joining of the top portion and the bottom portion at the second end to provide for separation of the top portion and the bottom portion upon aplication of the force.

7. Packaged cuvettes according to claim 6, wherein each cuvette has multiple reservoirs and windows arranged side-by-side and the openings of the reservoirs form the top surface of the composite structure and the windows of the first and last cuvette of the composite structure form the end walls.

8. Packaged cuvettes according to claim 7, wherein the removable supporting web comprises paper or a plastic film.

9. A method for inserting a plurality of cuvettes into a clinical analyzer comprising:
   providing packaged cuvettes according to claim 6;
   inserting the packaged cuvettes into a cuvette loading station of a clinical analyzer in a manner in which the tab remains accessible to application of a force;
   securing the packaged cuvettes in the loading station;
   applying a force to the tab in a direction toward the first end to peel back the support from the cuvettes; and
   removing the support to provide individual cuvettes.

10. A method according to claim 9, wherein the removable support comprises a web having a top and bottom portion, wherein the top portion contains an adhesive which contacts the top surface of the composite structure to anchor the individual cuvettes to the support and the bottom portion of the web contains no adhesive, wherein the top portion contacts the end walls of the composite article and the top portion and bottom portion are joined at the bottom of the end walls at the first and second ends and the web has a perforation in the vicinity of the second end where the top and bottom portions of the web are joined, wherein the method further comprises;

separating top and bottom portion of the web at the perforation;

applying a force to the tab to pull the bottom portion of the web toward the first end away from the bottom of the composite structure; and further applying a force to the tab to peel back to top portion of the web away from the top of the composite structure in a direction toward the second end.

11. A method according to claim 9, wherein the removable support comprises a web having a top and bottom portion, the top portion containing an adhesive which contacts the top surface of the composite structure to anchor the individual cuvettes to the support and the top portion contacts the end walls of the composite article, wherein the bottom portion of the web is divided into a first portion which extends from the first end to the second end and a second portion that doubles back on the first portion from the second end back to the first end, and wherein an adhesive is located on the first portion to contact the bottom surface of the composite structure, wherein the top portion and bottom portion are joined at the bottom of the end walls at the first and second ends, and the tab comprises a lower tab connected to the bottom portion of the web and an upper tab connected to the top portion of the web; wherein the method further comprises:

applying a force to the bottom tab to peel the bottom portion of the web toward the first end away from the bottom of the composite structure; and further applying a force to the top or bottom tab to peel back to top portion of the web away from the top of the composite structure in a direction toward the second end.

* * * * *